United States Patent [19]

Sugam et al.

[11] Patent Number: 4,686,853
[45] Date of Patent: Aug. 18, 1987

[54] METHOD FOR THE PREDICTION AND DETECTION OF CONDENSER FOULING

[76] Inventors: Richard J. Sugam, 5 Hoagland Rd., Flemington, N.J. 08822; Herbert S. Arnold, 2 Knapp Ave., Florham Park, N.J. 07932

[21] Appl. No.: 745,668

[22] Filed: Jun. 17, 1985

[51] Int. Cl.$^4$ ............................................. G01N 17/00
[52] U.S. Cl. ..................................... 73/61.2; 165/11.1
[58] Field of Search ................. 73/61.2, 112; 165/11.1

[56] References Cited

U.S. PATENT DOCUMENTS

| | | | |
|---|---|---|---|
| 3,552,189 | 1/1971 | Courvoisier et al. | 73/61.2 |
| 4,044,605 | 8/1977 | Bratthall | 73/61.2 |
| 4,176,544 | 12/1979 | Eyles et al. | 73/61.2 |
| 4,339,945 | 7/1982 | Knudsen et al. | 73/61.2 |
| 4,346,587 | 8/1982 | Brindak | 73/61.2 |
| 4,521,864 | 6/1985 | Characklis | 73/61.2 |

FOREIGN PATENT DOCUMENTS 2068540  8/1981  United Kingdom ................. 73/61.2

OTHER PUBLICATIONS

"Use of Pilot Scale Condensers For Biofouling Measurement And Control" C. R. Guerra et al. (1980).

Primary Examiner—Michael J. Tokar
Assistant Examiner—Hezron E. Williams

[57] ABSTRACT

A method for the detection of waterside fouling conditions in plant condensers and the differentiation between types of fouling conditions is described. The operating conditions of a pilot scale condenser are continuously matched to the dynamic operating conditions of a plant condenser and performance features (such as OHTR and pressure drop) are monitored and compared, thereby indicating to the plant operator whether fouling is occuring and, if so, whether there is macrofouling or microfouling.

10 Claims, 5 Drawing Figures

METHOD FOR THE PREDICTION AND DETECTION OF CONDENSER FOULING

BACKGROUND OF THE INVENTION

Large heat exchangers or condensers are used in a variety of applications. One of the more common uses of these devices is in electric power plants. Condensers are used in these plants to condense steam which has been generated in boilers and passed through turbines. Typically, cool water is continuously passed through an array of sealed tubes and the steam is directed to flow around and between the tubes of cool water. This results in condensing of the steam to water.

In most cases, the cooling water which is used in these condensers is drawn from an open body of water such as a lake or a river. The cooling water, as drawn from its source, contains a variety of troublesome inclusions and solutes.

Among the inclusions found in these waters are microorganisms and trash. The word "trash", as used here, refers to items of such gross size and composition that they can cause clogging if they are permitted to enter the system. This sort of clogging is known as macrofouling. Examples of trash include pieces of wood, tires, dead fish and the like. Most condenser systems use trash screens or racks at the cooling water intake point to prevent the entry of trash into the cooling water system. Unfortunately, even the best of such systems allow some trash to enter the system and this trash accumulates in the area of the inlets to the array of condenser tubes. This blocks the tubes and renders them nonfunctional. The condenser must then be shut down, drained and cleaned by hand, an unpleasant and time-consuming task.

Microorganisms are, of course, present in all natural waters. Some of these microorganisms thrive in the warm environment of the condenser tubes. These microorganisms tend to adhere to the inside surface of the condenser tubes and multiply rapidly. If this process is allowed to continue, the bore of the condenser tube will eventually become occluded and its heat transfer function will be impaired. This is known as biological fouling or biofouling. Presently, it is common practice to add anti-biofouling agents, such as chlorine to the cooling water to retard the growth of these organisms. Often, these agents must be used well in excess of need in order to provide a reasonable margin of safety. This results in waste of expensive materials and the discharge of substantial quantities of these materials into the environment.

Cooling water also contains inorganic salts and other compounds which contribute to the build-up of scale on the inside of the condenser tubes. Scale formation, like biofouling can result in diminished heat transfer and the gradual occlusion of the bore of the condenser tubes. This process of gradual occlusion by biofouling and scale formation is known as microfouling.

The accurate prediction and detection of macrofouling and microfouling is a matter of some importance. If these problems can be dealt with in their incipiency, plant down-time and damage to the condenser can be avoided or minimized. Also, more accurate measurement and prediction techniques can make possible a reduction in the safety margin which must be allowed in the application of microfouling control agents.

Previously, fouling of the condenser had been inferred from an increase in the force necessary to pump cooling water through the plant condenser. This technique does not permit the detection or prediction of fouling at an early stage. It is also unable to consistently differentiate between macrofouling and microfouling. A large number of extraneous factors can influence these sorts of measurements when they are made in a plant-scale condenser. Thus, it is at best only an approximate indication of the fouling behavior of the plant condenser. Two other techniques which have been used are removing the condenser from service for visual inspection of the tubes, and monitoring turbine back pressure, circulating water temperature and the unit electrical output while the condenser is in service and comparing these three parameters to an established baseline. None of these techniques have been entirely satisfactory.

It has been known to use pilot-scale condensers to measure Overall Heat Transfer Resistance (OHTR) and to use these devices to predict microfouling. These devices are set to operate under constant conditions which are thought to be representative of plant conditions. The OHTR is calculated by well-known methods from several factors including the temperature of input and output water, the velocity of the cooling water and several others. Thus, variations in OHTR can be due to factors other than the fouling condition. These other factors can be significant in plant condensers. Because of the smaller size of pilot plants, their OHTR's are not so greatly influenced by uncontrollable variations in these factors and are thought to be useful models of plant condenser microfouling activity. However, there are limitations on the usefulness of this technique. For example, the OHTR can actually be decreased as a result of the early stages of microfouling. This can be misleading and demonstrates the limited usefulness of this technique in the early detection of microfouling. Also, OHTR measurements give little or no guidance as to whether macrofouling is developing.

The measurement of the cooling water pressure drop across the plant condenser tubes as a fouling indicator has been considered but thought to be even less useful than OHTR measurement in pilot condensers as a tool for predicting and detecting microfouling. Pressure drop measurements in plant condensers were thought to be subject to far too many variables to be measured accurately or to be useful predictions of microfouling. Guerra, et al. *Use of Pilot Scale Condensers for Biofouling Measurement and Control* (1980) gave some indication that the pressure drop across the pilot-scale condenser could be measured with sufficient accuracy to be useful in the prediction of microfouling. However, Guerra, et al. were never able to observe a pilot-scale condenser whose pressure-drop behavior tracked or predicted the pressure-drop behavior of a fouling plant condenser. Also, Guerra et al. were unable to distinguish between macrofouling and microfouling.

SUMMARY OF THE INVENTION

It has now been discovered that the simultaneous observation of the pressure drop across the condenser tubes of a plant condenser and a pilot condenser not only provides an unexpectedly accurate means of predicting and detecting condenser fouling but also permits the reliable identification of the fouling as either macrofouling, microfouling or a combination of both microfouling and macrofouling.

In the present method the baseline pressure drop across a clean plant condenser and a clean pilot condenser are established. The two condensers are then operated in parallel under the same operating conditions. The pilot condenser should be operated so as to track changes in the operating conditions of the plant condenser. This can advantageously be done by the use of computerized controls which continuously monitor and update the status of the condenser. A simultaneous and proportional increase in the pressure drop across both units can be reliable indicator of microfouling. An increase in the pressure drop across only one condenser will indicate that the condenser where the magnitude of the pressure drop increases is experiencing trash fouling. A simultaneous but non-proportional increase in the pressure drop across both units will indicate that both units are experiencing microfouling and that the unit with the greatest change in pressure drop is also experiencing trash fouling.

In one embodiment of this invention the OHTR in the pilot condenser is monitored in addition to the pressure drop across the plant and pilot condensers. The OHTR is monitored in a conventional manner and the resulting data is used to provide an additional indication of the condition of the condenser. The concurrent use of these two techniques, results in a heretofore unattainable predictive accuracy.

The method of the present invention therefore provides a new and reliable technique for monitoring and predicting condenser fouling and provides the first known practical technique for differentiating between macrofouling and microfouling.

DETAILED DESCRIPTION OF THE INVENTION

Figure 1:
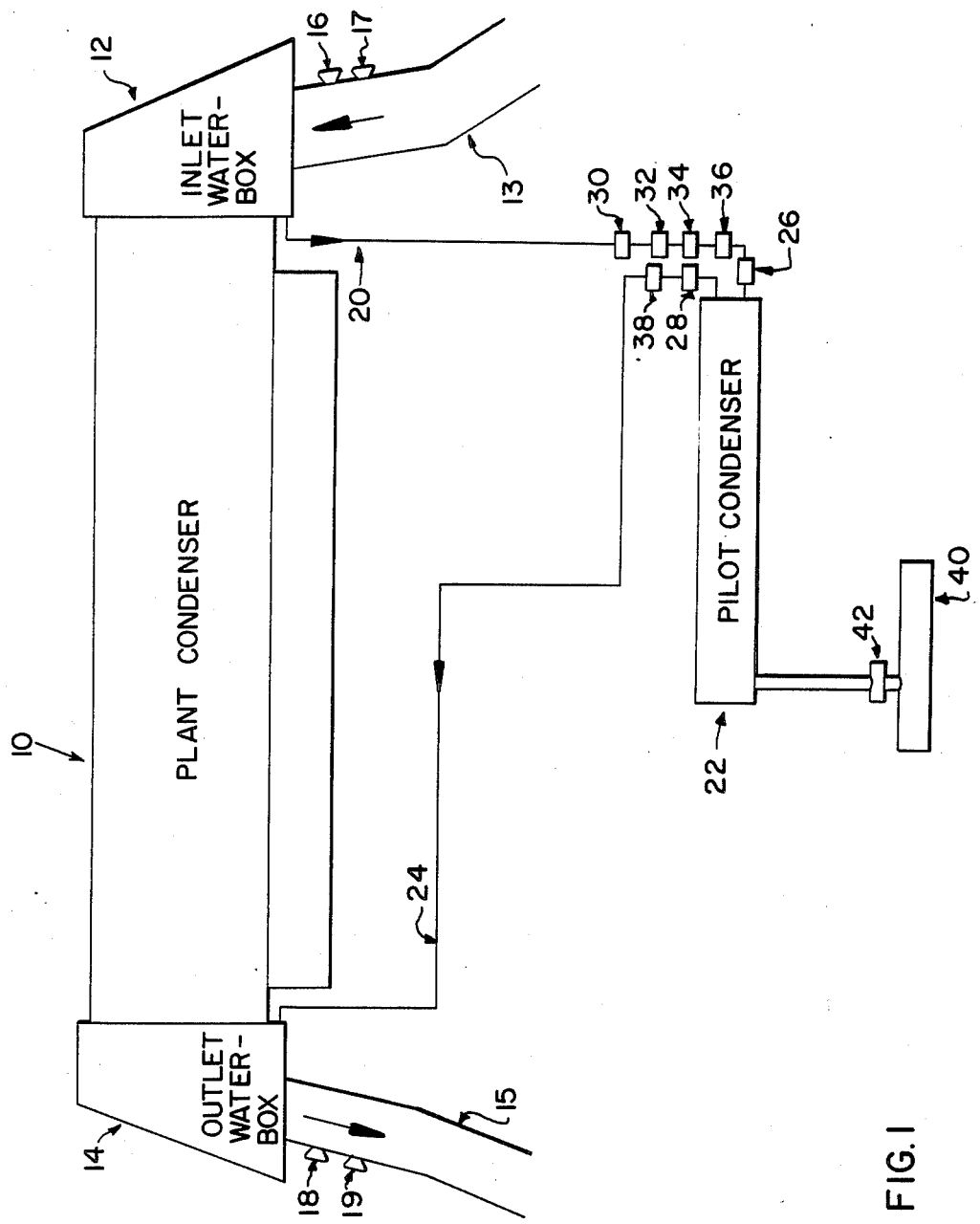
FIG. 1 illustrates a condenser system suitable for use in the process of the invention.

In the method of the present invention a pilot scale condenser is used in the prediction and detection of plant fouling. This condenser should be of a design suited to approximate the environment of the cooling water side of the plant condenser. It is not necessary that the conditions of the steam or "shell" side of the plant condenser be duplicated in the pilot condenser. This is so because shell side fouling is distinct from cooling water side fouling and it is dealt with on a different basis. It is therefore not of great interest in this situation.

The cooling water side conditions of the plant condenser may be said to be adequately approximated by the pilot condenser when the water velocity through the two consensors are approximately the same, the inlet cooling water temperature of the two condensers are approximately the same, the outlet water temperatures of the two condensers are also approximately the same and the dimensions of the condenser tubes are approximately the same.

The pilot condenser will, of course, ordinarily have fewer condenser tubes than the plant condenser. The composition, length and diameter of the condenser tubes in the two condensers should also be similar. The condenser tubes in the pilot condenser may be "folded" into a multiple-pass arrangement in order to make the size of the pilot condenser more manageable. Folding will result in an increased pressure drop across the condenser tubes, however, this is acceptable since the method of this invention is concerned with deviation of the pressure drop from a baseline value.

Other plant operating conditions which may be approximated in the pilot condenser include the type and concentration of anti-microfouling agents which are added to the cooling water. When the plant condenser is removed from service or de-watered, the same can be done to the pilot condenser. Also, whenever the plant condenser is cleaned to remove microfouling material such as by the use of brushes, acid solutions or high pressure water, the same operation should be performed on the pilot condenser. This should include both on-line and off-line condenser cleaning operations.

While the present method may be successfully carried out when the pilot condenser is operated at conditions which are initially fixed to conditions that are generally representative of plant condenser operating conditions, the accuracy and reliability of the method of this invention increases when the operating conditions of the pilot condenser are frequently adjusted so as to maintain them in close approximation to those of the plant condenser. This may be accomplished by frequent manual adjustments or, preferably, by the use of automatic sensors in the plant condenser which provide data to a computer which constantly regulates the pilot condenser's operation.

When the operating conditions of the two condensers have been suitably matched, baseline pressure drop values should be established. This will usually involve the operation of the condenser units for a sufficient time to reach a steady state of isothermal heat exchange and the collection of a representative amount of baseline data. The amount of time and data required will vary with the specific condensers used, but will be readily ascertainable to one of skill in the art.

Once baseline pressure drop values for the plant and pilot condensers have been established, the pressure drops can be monitored for indications of fouling. Any significant increase in the pressure drop in the condensers indicates that fouling may be occurring. Any change in the pressure drop from the baseline which is greater than the error of the pressure measurement device which is employed is significant.

Microfouling is usually a slow, gradual process and is indicated by a slow, gradual increase in the pressure drop in both condensers. Macrofouling is usually a more rapidly developing phenomenon than microfouling. Typically, clean, clear tubes will be suddenly occluded by dead fish or the like. This will generally result in a sharper, more rapid change in pressure drop and will not be seen in both condensers (i.e., macrofouling will be seen only in the condenser where the dead fish are caught in the condenser tubes). Thus, by monitoring the pressure drop across the plant and pilot condenser, microfouling and macrofouling can be both detected and distinguished.

In a particularly advantageous embodiment of this invention the pilot condenser inlet cooling water is continuously screened by means of an additional screening device and the screening device is frequently cleaned or replaced. This can be done so as to effectively eliminate the possibility of macrofouling in the pilot condenser and also eliminates the possibility that the pilot and plant condensers will be simultaneously macrofouled.

It has also been observed that the OHTR of the pilot condenser may be monitored as part of the process of the present invention in order to provide confirmation of the indications provided by the pressure drop measurements. This simultaneous monitoring of these two parameters provides an even more reliable indication of the microfouling condition of the plant condenser.

Turning now to FIG. 1 we see an illustration of a condenser system which is suitable for use in the process of the present invention. The plant condenser 10 has a cooling water inlet box 12, a cooling water outlet box 14 and steam inlets and outlets (not shown). Inlet box 12 and outlet box 14 are fed by inlet pipe 13 and outlet pipe 15 respectively. Pressure probes 16 and 18 are located at pipes 13 and 15 respectively. Temperature probes 17 and 19 are also provided at inlet pipe 12 and outlet pipe 15 respectively. Within the condenser is an array of condenser tubes (not shown) through which the cooling water passes during the operation of the condenser. A pilot condenser cooling water supply line 20 draws cooling water from inlet box 12 and supplies cooling water to the pilot condenser 22. Within the pilot condenser 22 is an array of condenser tubes (not shown). These tubes are about the same length as the condenser tubes in the plant condenser but are folded within the pilot condenser. The tubes in this illustration are folded an even number of times and the outlets and inlets are therefore on the same end of the condenser. A pilot condenser cooling water return line 24 returns the used cooling water to the outlet box 14. Pressure probes 26 and 28 are provided at the cooling water inlet and outlet respectively of the pilot condenser 22. A strainer 30, a pump 32 and a flow controller 34 are located at the cooling water inlet of the pilot condenser 22. Temperature probes 36 and 38 are provided at the cooling water inlet and outlet respectively. A heating unit 40 provides hot water to the pilot condenser 22. The hot water is circulated through the pilot condenser 22 by a pump 42. The hot water circuit may be provided with suitable temperature, flow and pressure control devices.

When this apparatus is operated in accordance with the present invention, the plant condenser is operated as usual and the pilot condenser is operated so that a steady rate, isothermal heat exchange takes place. The temperature of the water in inlet 20 and inlet box 12 should be approximately equal as should the temperature of the water in outlet 24 and outlet box 14. The pressure drop across the condenser tubes of pilot condenser 22 and plant condenser 10 are measured and base line values for each condenser are established.

Figure 2:
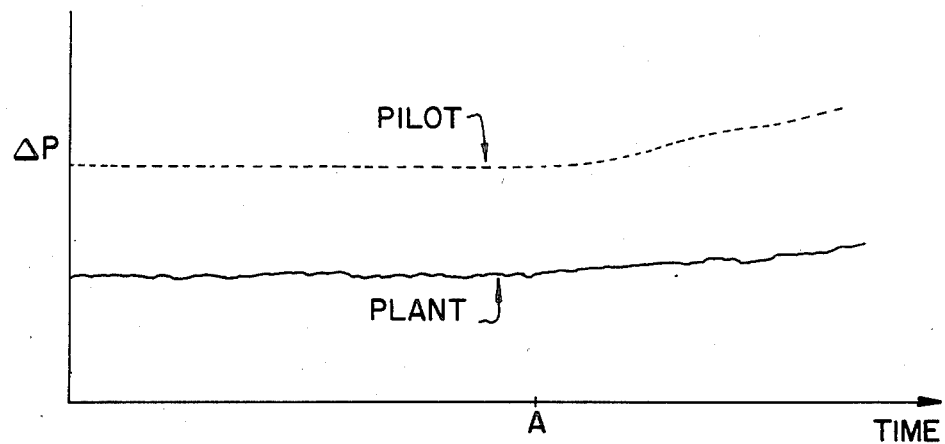
FIGS. 2-4 illustrate plots of pressure drop verses time data.

FIG. 2, which is a plot of pressure drop versus time illustrates how this data is used in the present process. The solid line represents the pressure drop in the plant condenser 10 and the dashed line represents the pressure drop in the pilot condenser 22. Following these plots through time, one may see that baseline values are first established. Later, an increase in the pressure drop of both units is seen at about time A. This indicates that both units have begun to experience microfouling. The degree of fouling at time A is probably not yet detrimental to the operation of the plant condenser but the plant operator now has an early warning of microfouling.

Figure 3:
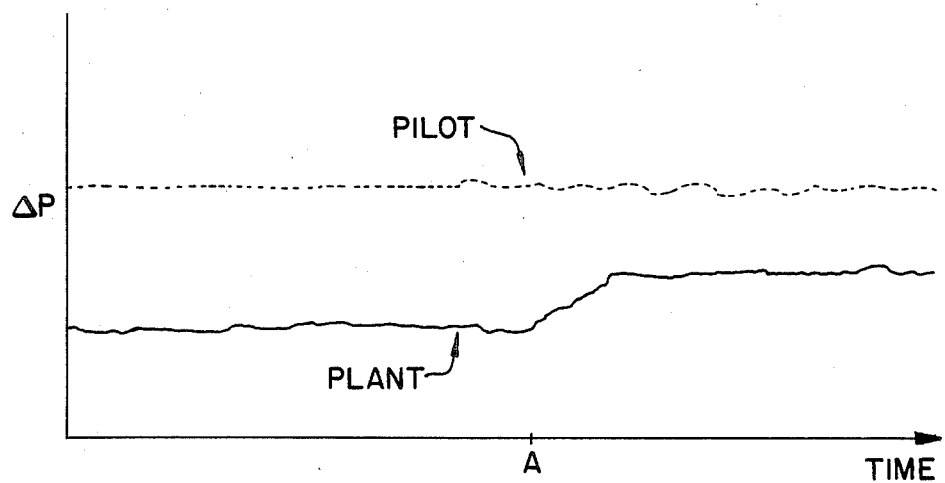

FIG. 3 represents the pressure drop data obtained under different circumstances. Following this plot through time we see the establishment of baseline values. Then, at about time A, the pressure drop across the plant condenser increases while the drop across the pilot condenser 22 remains steady. This indicates that the screening of the condenser cooling water has been ineffective and that macrofouling of the plant condenser 10 has occured.

Figure 4:
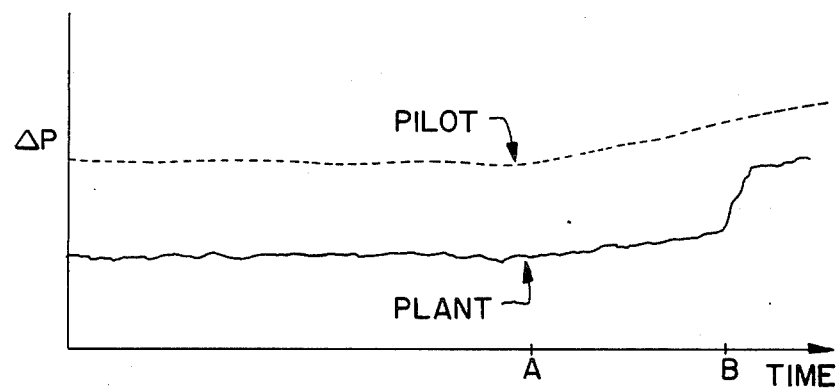

FIG. 4 illustrates yet another operating condition. As the plot is followed across time, we see that the pressure drops across the condensers first reaches baseline values and then, at time A, both plots show an increase in pressure drop just as was seen in FIG. 2. Then, at time B, the plant condenser displays a jump in pressure drop. This data indicates that both units are experiencing microfouling and that, as of about time B, the plant condenser is also experiencing macrofouling.

Figure 5:
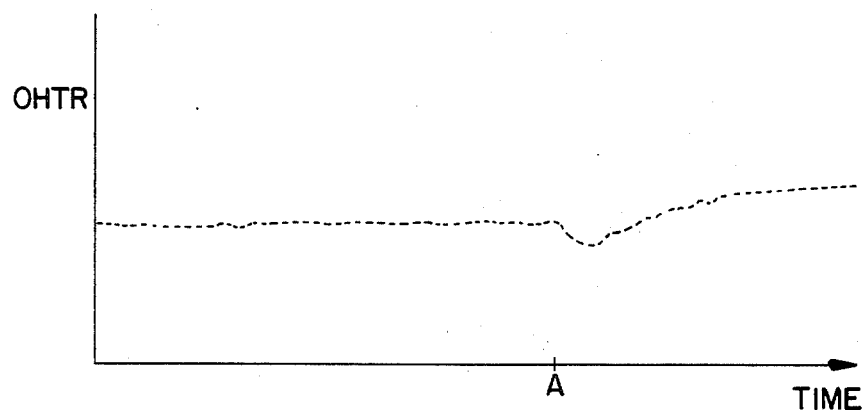
FIG. 5 illustrates a plot of OHTR verses time of the pilot condenser.

FIG. 5 illustrates the use of the OHTR of the pilot condenser 22 as an additional indicator of microfouling. In FIG. 4, which represents data obtained under conditions which are the same as those illustrated in FIG. 2, the OHTR of the pilot condenser 22 is plotted versus time. As the system is operated a shift in the OHTR is seen at time A, which corresponds to time A in FIG. 2. This provides independent confirmation that microfouling is occuring and makes such a judgment possible on the basis of far subtler changes in the data than would be possible if either one of these indicators were used alone. The OHTR may be determined in a conventional manner, such as is described in Guerra, et al. supra. It will be appreciated that the OHTR should be determined under such conditions that changes in the OHTR will reflect changes in the fouling condition of the condenser and not changes in the other variables which can influence the OHTR.

It will be understood that the present invention is defined by the claims and is not limited to the embodiment specifically discussed herein.

We claim:

1. A method for the prediction and detection of fouling of condenser tubes during the operation of a condenser comprising:
    measuring the drop in pressure across the condenser tubes of a substantially clean, unfouled main condenser unit to establish a baseline cooling water pressure drop for the main condenser unit; and
    measuring the drop in pressure across the condenser tubes of a substantially clean, unfouled pilot-scale condenser unit which is operated so as to approximate the environment on the cooling water side of the plant condenser to establish a baseline cooling water pressure drop for the pilot-scale condenser unit; and
    operating said main condenser unit and said pilot-scale condenser unit while continuously measuring the pressure drop across each unit such that an approximately simultaneous and proportional increase in pressure drop across both the main condenser and the pilot-scale condenser indicates that the condenser tubes are becoming microfouled and that an increase in pressure drop across only one unit indicates that only the unit demonstrating the increased pressure drop is subject to macrofouling and an approximately simultaneous but significantly disproportionate pressure drop in both units indicates that (1) both units are becoming microfouled and (2) the unit with the greater increase in pressure drop is also subject to macrofouling.

2. The method of claim 1 wherein said pilot-scale condenser unit draws cooling water from the cooling water inlet of said main condenser and discharges its cooling water into the outlet of the main condenser.

3. The method of claim 1 wherein the operating conditions of the pilot-scale condenser are continuously adjusted so as to conform to the operating conditions of the main condenser and wherein the condenser tubes of both condensers are subjected to the same cleaning treatments to remove microfouling materials.

4. The method of claim 3 wherein the operating conditions are selected from the group consisting of: the condenser cooling water outlet temperature, concentration of microfouling control agents in the cooling water and the type of microfouling control agents in the cooling water.

5. The method of claim 1 comprising the further steps of:
straining the cooling water entering said pilot-scale condenser and;
removing promptly all material strained out of the water entering the pilot-scale condenser such that no macrofouling material is permitted to accumulate in the pilot condenser unit.

6. The method of claim 1 comprising the further steps of:
calculating the OHTR of the substantially clean, unfouled pilot-scale condenser to establish a baseline OHTR for the pilot-scale condenser and;
continuously calculating the OHTR of the pilot-scale condenser during its operation such that any change in the OHTR of the pilot condenser indicates a change in the fouling condition of the condenser.

7. The method of claim 2 when the operating conditions of the pilot-scale condenser are continuously adjusted so as to conform to the operating conditions of the main condenser and wherein the condenser tubes of both condensers are subjected to the same cleaning treatments to remove microfouling materials.

8. The method of claim 7 wherein said operating conditions are selected from the group consisting of: the condenser cooling water outlet temperature, the concentration of microfouling control agents in the cooling water and the type of microfouling control agent in the cooling water.

9. The method of claim 7 comprising the further steps of:
straining the cooling water entering said pilot-scale condenser and;
removing promptly all material strained out of the water entering the pilot-scale condenser such that no microfouling is permitted to accumulate in the pilot condenser unit.

10. The method of claim 7 comprising the further steps of:
calculating the OHTR of the substantially clean, unfouled pilot-scale condenser to establish a baseline OHTR for the pilot-scale condenser;
continuously calculating the OHTR of the pilot-scale condenser during its operation such that any change in the OHTR of the pilot condenser indicates a change in the fouling condition of the condenser.

* * * * *